(12) United States Patent
Chauhan et al.

(10) Patent No.: US 11,963,936 B2
(45) Date of Patent: Apr. 23, 2024

(54) METHOD OF MANUFACTURING STABLE EMULSIONS AND COMPOSITIONS CONTAINING THE SAME

(71) Applicant: UNIVERSITY OF FLORIDA RESEARCH FOUNDATION, INC., Gainesville, FL (US)

(72) Inventors: Anuj Chauhan, Gainesville, FL (US); Robert A. Damitz, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 270 days.

(21) Appl. No.: 17/456,956

(22) Filed: Nov. 30, 2021

(65) Prior Publication Data

US 2022/0079890 A1    Mar. 17, 2022

Related U.S. Application Data

(62) Division of application No. 15/028,496, filed as application No. PCT/US2014/059819 on Oct. 9, 2014, now Pat. No. 11,219,606.

(60) Provisional application No. 61/889,885, filed on Oct. 11, 2013.

(51) Int. Cl.
| | | |
|---|---|---|
| *A61K 31/05* | (2006.01) | |
| *A61K 9/00* | (2006.01) | |
| *A61K 9/107* | (2006.01) | |
| *A61K 47/10* | (2017.01) | |
| *A61K 47/14* | (2017.01) | |
| *A61K 47/44* | (2017.01) | |

(52) U.S. Cl.
CPC ............ *A61K 31/05* (2013.01); *A61K 9/0019* (2013.01); *A61K 9/107* (2013.01); *A61K 47/10* (2013.01); *A61K 47/14* (2013.01); *A61K 47/44* (2013.01)

(58) Field of Classification Search
CPC ...................................................... A61K 31/05
See application file for complete search history.

(56) References Cited

U.S. PATENT DOCUMENTS

| | | |
|---|---|---|
| 6,177,477 B1 | 1/2001 | George et al. |
| 6,267,985 B1 | 7/2001 | Chen et al. |
| 2002/0032171 A1 | 3/2002 | Chen et al. |
| 2004/0225022 A1 | 11/2004 | Desai et al. |
| 2006/0134145 A1 | 6/2006 | Matsuda et al. |
| 2009/0069445 A1* | 3/2009 | Takeda .................... A61P 25/04 514/731 |

FOREIGN PATENT DOCUMENTS

CN       102085185 A      6/2011

OTHER PUBLICATIONS

Giri et al., Prospective and Challenges of Micro-Emulsion as a Novel Carrier for Drug Delivery, 2013, Journal of PharmaSciTech, (2)2, pp. 56-61. (Year: 2013).
Gupta, et al. "Biocompatible Microemulsions and Their Prospective Uses in Drug Delivery" Journal of Pharmaceutical Sciences, vol. 97, No. 1, Jan. 2008; pp. 22-45.
International Search Report for International Application No. PCT/US2014/059819; International Filing Date Oct. 9, 2014; Report Mail Date Jan. 28, 2015 (6 pages).
Warisnoicharoen, et al. "Nonionic oil-in-water microemulsions: the effect of oil type on phase behaviour" International Journal of Pharmaceutics 198 (2000) 7-27.
Written Opinion for International Application No. PCT/US2014/059819; International Filing Date Oct. 9, 2014; Report Mail Date Jan. 28, 2015 (8 pages).

* cited by examiner

*Primary Examiner* — Rei Tsang Shiao
(74) *Attorney, Agent, or Firm* — Thomas | Horstemeyer, LLP

(57) ABSTRACT

Disclosed herein is a composition comprising a biologically active agent; a base oil; an additional oil that is soluble in the base oil with a partition coefficient for the biologically active molecule that is at least twice that of the base oil; where the base oil and the additional oil are present in the composition in an amount effective to reduce the amount of the biologically active agent in an aqueous phase to less than 80 wt % of the amount with just the base oil present in an otherwise identical composition at the same total oil loading; a nonionic surfactant; and water.

16 Claims, 9 Drawing Sheets

(A) (B)

METHOD OF MANUFACTURING STABLE EMULSIONS AND COMPOSITIONS CONTAINING THE SAME

CROSS-REFERENCE TO RELATED APPLICATIONS

This disclosure is a divisional application of U.S. Non-Provisional application Ser. No. 15/028,496 filed on Apr. 11, 2016, which claims priority to International Application No. PCT/US14/059819 filed on Oct. 9, 2014, which claims the benefit of U.S. Provisional Application No. 61/889,885 filed on Oct. 11, 2013, the entire contents of each of which are hereby incorporated by reference.

BACKGROUND

Medications containing biologically active agents are often administered intravenously as oil-in-water (O/W) emulsions. A significant concentration of these biologically active agents remain in free form in the emulsion aqueous phase and this free form often is injurious to the patient in that it often causes discomfort. The free biologically active agent concentration of an emulsion system is driven by its solubility equilibrium. After injection, it is the free biologically active agent concentration (that is present in the aqueous phase) which makes immediate contact with the vasculature leading to significant tissue irritation and damage. It is therefore useful to reduce the aqueous phase biologically active agent concentration to as low as practically possible.

It is therefore desirable to reduce the free biologically active agent concentration in emulsion formulations while at the same time maintaining acceptable emulsion stability.

SUMMARY

Disclosed herein is a composition comprising a biologically active agent; a base oil; an additional oil that is soluble in the base oil with a partition coefficient for the biologically active molecule that is at least twice that of the base oil; where the base oil and the additional oil are present in the composition in an amount effective to reduce the amount of the biologically active agent in an aqueous phase to less than 80 wt % of the amount with just the base oil in an otherwise identical composition at the same total oil loading; a non-ionic surfactant; and water.

Disclosed herein too is a composition comprising a biologically active agent; a first oil; where the first oil comprises at least one triglyceride; a second oil; a non-ionic surfactant; and water; where the composition is an emulsion; where the first oil and the second oil are present in the composition in an amount effective to reduce the amount of the biologically active agent in an aqueous phase to less than 80 wt % of the amount with just the first oil present while maintaining or improving the kinetic stability of the emulsion in an otherwise identical composition at the same total oil loading.

Disclosed herein too is a composition comprising propofol; soybean oil; ethyl butyrate; where the soybean oil and the ethyl butyrate are present in the composition in an amount effective to reduce the amount of propofol in an aqueous phase to less than 20 milligrams per liter; a non-ionic surfactant; and water.

Disclosed herein too is a method of manufacturing a composition comprising mixing a biologically active agent; a first oil; where the first oil comprises at least one triglyceride; a second oil; a non-ionic surfactant; and water to form an emulsion; where the first oil and the second oil are present in the composition in an amount effective to reduce the amount of the biologically active agent in an aqueous phase to less than 80 wt % of the amount with just the first oil present while maintaining or improving the kinetic stability of the emulsion in an otherwise identical composition at the same total oil loading.

Disclosed herein too is a method of using a composition comprising administering to a living being a composition comprising a biologically active agent; a base oil; a fatty acid and/or an ester of a fatty acid; where the base oil and the fatty acid and/or the ester of the fatty acid are present in the composition in an amount effective to reduce the amount of the biologically active agent to less than 20 milligrams per liter; a non-ionic surfactant; and water.

Disclosed herein too is a method of using a composition comprising administering to a living being a composition comprising propofol; a base oil; a fatty acid and/or an ester of a fatty acid; where the base oil and the fatty acid and/or the ester of the fatty acid are present in the composition in an amount effective to reduce the amount of propofol to less than 20 milligrams per liter; a non-ionic surfactant; and water.

Figure 9A:
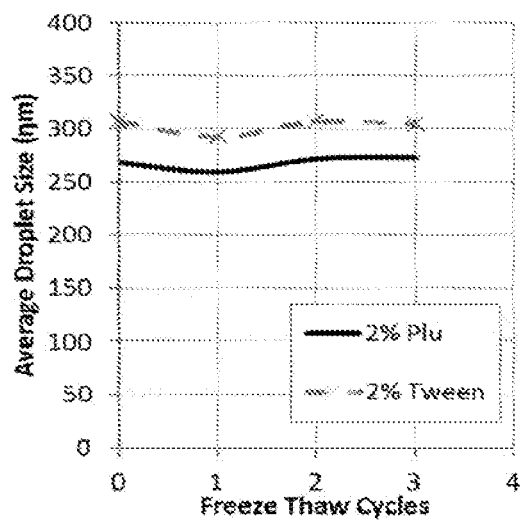
Figure 9B:
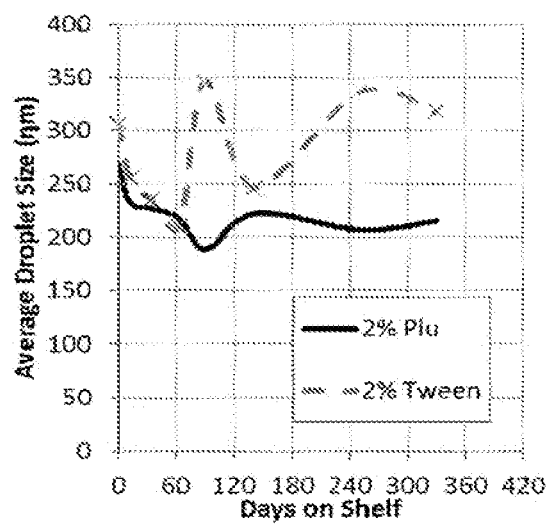

contain 1 wt % propofol, 5 wt % soybean oil, 5 wt % ethyl butyrate, 1 wt % Pluronic F68, and $10^{-4}$ wt % sodium stearate;

FIG. 9(A) is a graph showing average droplet sizes without and ionic surfactant for the different emulsions after several freeze-thaw cycles;

FIG. 9(B) is a graph showing shelf life for the emulsions of the FIG. 9(A). All formulations contain 1 wt % propofol, 10 wt % soybean oil, and no ionic surfactant.

DETAILED DESCRIPTION

Propofol (2,6-diisopropylphenol), a common anesthetic administered intravenously, is formulated as oil-in-water (O/W) emulsions. An emulsion is a mixture of immiscible oil and aqueous phases stabilized by surfactant molecules. Commercially-available emulsions of propofol also known as Diprivan are prepared with 1% (w/v) propofol dissolved in 10% soybean oil. Diprivan is stabilized with 1.2% egg lecithin surfactant and 0.005% sodium EDTA as a preservative. Diprivan is notable for causing significant patient pain on injection which is partially attributed to the free drug concentration, or the partition of drug which dissolves in the emulsion aqueous phase.

The free drug concentration of an emulsion system is driven by its solubility equilibrium. Propofol is poorly soluble in water at 150-180 micrograms per milliliter (μg/mL). While a majority of the drug in Diprivan is encapsulated in the oil phase, the propofol concentrations in the aqueous phase have been observed to be as high as 12.4 μg/mL. It is known that sterically-hindered phenolic compounds such as propofol are biological membrane irritants. After injection, it is the aqueous phase drug concentration which can make immediate contact with the vasculature leading to significant tissue irritation and damage. Thus, it is useful to reduce the aqueous phase drug concentration to as low as practically possible.

Emulsions are thermodynamically unstable giving them limited shelf life and risk for embolism when injected and thus kinetic stability for an extended period is desirable for any emulsion based drug delivery system. Microemulsions are a thermodynamically-stable subclass of emulsions that have greatly reduced interfacial tension and droplet sizes due to higher surfactant to oil ratios. Microemulsions have been considered for propofol delivery, but poor results were seen with elevated pain levels on injection of microemulsion propofol. The increase of pain in microemulsion propofol is attributed to elevated aqueous phase drug concentration of 83.9 μg/mL (4) and rapid rates of droplet dissolution in blood after injection due to their small droplet sizes.

Due to their thermodynamic instability, it is challenging to design a shelf-stable emulsion. Emulsions are subject to several destabilizing mechanisms including gravimetric settling, flocculation, coalescence, Ostwald ripening, creaming, and finally phase separation. Larger emulsion droplets are more susceptible to the more destructive mechanisms of creaming, gravimetric settling, and phase separation. Each of these destabilizing mechanisms has their own unique and complex driving forces. Compounded by these issues, the excipient oil and surfactants have strong effects on the resulting emulsion stability. Certain surfactants are more effective with some oil types but have little effect on other oil types. Thus, there is a very broad scope of emulsion design, and each ingredient changed may have profound effects on the stability of the formulation.

Several strategies can be employed to increase kinetic stability and maximize shelf life. Surfactants, in particular nonionic pluronic surfactants provide strong rigidity to the emulsion interface resulting in minimal surface deformation during collisions between neighboring droplets. Electrostatics and DLVO (Derjaguin and Landau, Verwey and Overbeek) theory suggests that electrostatic repulsion between droplets provides an energy barrier which deters neighboring droplets from approaching. Additives can be used to modify density or viscosity of each phase to resist gravimetric settling or reduce droplet collisions. Therefore, the goal of this study is twofold: 1) to reduce the free drug concentration in propofol emulsion formulations while 2) maintaining acceptable emulsion stability.

Disclosed herein is an aqueous emulsion composition that comprises two or more biocompatible fatty oils, water and one or more biologically active agents. The two or more biocompatible fatty oils preferably comprise a base oil and an additional oil (a fatty acid and/or an ester of a fatty acid), both of which are compatible with the human vasculature and which provide the composition with acceptable emulsion stability, where the fatty acid or the ester or the fatty acid has a lower number average molecular weight than the base oil. In one preferred embodiment, the base oil comprises at least one triglyceride while the fatty acid is simple fatty acid.

Alternatively, the composition may be described as being an emulsion that comprises a biologically active agent; a first oil, which is the base oil that stabilizes the emulsion and comprises at least one triglyceride; a second oil (also referred to herein as an additional oil), which is the fatty acid or the ester of a fatty acid and which reduces a free form of the biologically active agent to less than 80% of what it would be with just the first oil while maintaining or improving the kinetic stability of the emulsion in an otherwise identical composition based on the weight of the composition; a non-ionic surfactant; and water.

The presence of the two or more fatty oils in the composition increases emulsion stabilization while simultaneously preventing the biologically active agent from remaining in the free form in the aqueous phase. The higher molecular weight base oil generally stabilizes the emulsion (i.e., it facilitates retaining emulsion droplets in the micrometer size range and prevents the emulsion from separating into two macrophases) while the lower molecular weight fatty acid acts synergistically with the aqueous phase and the base oil to prevent the biologically active agent from remaining in the free form in the aqueous phase.

Examples of base oils derived from biological products are algae oil, animal fat oils and tallow, fish oils, vegetable oil, waste vegetable oil, or the like, or a combination comprising at least one of the foregoing base oils derived from biological products. Examples of oil derived from agricultural products are soybean oil, olive oil, rapeseed oil (canola), castor bean oil, sunflower seed oil, peanut oil, corn oil, safflower seed oil, linseed oil, jatropha oil, or the like, or a combination comprising at least one of the foregoing oils derived from agricultural products. Examples of oils derived from forest products are apricot seed oils, mango oil, coconut oil, cashew nut oil, or the like, or a combination comprising at least one of the foregoing oils derived from forest products.

It is desirable for the base oil to comprise at least one triglyceride. In one exemplary embodiment, the base oil comprises poly-unsaturates such as alpha-linolenic acid in an amount of 7 to 10 wt %, linoleic acid in an amount of 45 to 55 wt %; and a mono-unsaturate such as oleic acid in an amount of 18 to 28 wt %, based on the total weight of the base oil. It also desirable for the base oil to have saturated fatty acids such as stearic acid in an amount of 2 to 6 wt %, and palmitic acid in an amount of 7 to 13 wt %, based on the total weight of the base oil. In an exemplary embodiment, the base oil is soya bean oil. The base oil is present in an amount of 1 to 30, preferably 2 to 20 and preferably 3 to 10 weight percent (wt %), based on the total weight of the composition.

The fatty acid is compatible with the base oil and functions to prevent the biologically active agents from staying in water in the free form. The fatty acid is generally a simple fatty acid having a carboxylic acid with a long aliphatic tail (chain), which is either saturated or unsaturated. Most fatty acids have a chain of an even number of carbon atoms from 2 to 28. Fatty acid chains differ by length, often categorized as short to very long. Short-chain fatty acids (SCFA) are fatty acids with aliphatic tails of fewer than six carbons (i.e. butyric acid. Medium-chain fatty acids (MCFA) are fatty acids with aliphatic tails of 6-12 carbons, which can form medium-chain triglycerides. Long-chain fatty acids (LCFA) are fatty acids with aliphatic tails 13 to 21 carbons. Very long chain fatty acids (VLCFA) are fatty acids with aliphatic tails longer than 22 carbons. In an exemplary embodiment, the simple fatty acid has a carboxylic acid group and a single chain of 2 to 28 carbon atoms.

The simple fatty acids used in the composition are in either acid form or in the ester form. The ester form is obtained by reacting alcohols with carboxylic acids. The fatty acids are carboxylic acids. Examples of carboxylic acids are methanoic acid, ethanoic acid, propanoic acid, butanoic acid, pentanoic acid, hexanoic acid, heptanoic acid, octanoic acid, nonanoic acid, decanoic acid, undecanoic acid, dodecanoic acid, tridecanoic acid, tetradecanoic acid, pentadecanoic acid, hexadecanoic acid, heptadecanoic acid, octadecanoic acid, icosanoic acid, or the like. Examples of alcohols that can be reacted with the carboxylic acids to produce the esters are methanol, ethanol, propanol, butanol, pentanol, hexanol, heptanol, octanol, nonanol, decanol, undecanol, dodecanol, tridecanol, tetradecanol, pentadecanol, hexadecanol, heptadecanol, octadecanol, icosanol, or the like. In a preferred embodiment, the number of carbon atoms on the fatty acid is 3 to 7.

Examples of simple fatty acid esters that may be used in the composition are allyl hexanoate, benzyl acetate, bornyl acetate, butyl acetate, butyl butyrate, butyl propanoate, ethyl acetate, ethyl butyrate, ethyl hexanoate, ethyl cinnamate, ethyl formate, ethyl heptanoate, ethyl isovalerate, ethyl lactate, ethyl nonanoate, ethyl pentanoate, geranyl acetate, geranyl butyrate, geranyl pentanoate, isobutyl acetate, isobutyl formate, isoamyl acetate, isopropyl acetate, linalyl acetate, linalyl butyrate, linalyl formate, methyl acetate, methyl anthranilate, methyl benzoate, methyl butyrate, methyl cinnamate, methyl pentanoate, methyl phenylacetate, methyl salicylate, nonyl caprylate, octyl acetate, octyl butyrate, amyl acetate, pentyl butyrate, pentyl hexanoate, pentyl pentanoate, propyl acetate, propyl hexanoate, propyl isobutyrate, terpenyl butyrate, or the like. A preferred simple fatty acid ester is ethyl butyrate.

The fatty acid is present in an amount of 1 to 30, preferably 2 to 20 and preferably 3 to 10 weight percent (wt %), based on the total weight of the composition.

In one embodiment, the fatty acid is used in the composition in a 4:6 to 6:4 weight ratio, preferably 4.5:5.5 to 5.5:4.5 weight ratio and most preferably 1:1 weight ratio with the base oil.

The water may be present in the composition in an amount of 1 to 95 wt %, preferably 30 to 93 wt % and more preferably 50 to 90 wt %, based on the total weight of the composition. Deionized water is preferred.

The composition may include biologically active agents including anti-proliferative/antimitotic agents including natural products such as vinca alkaloids (e.g., vinblastine, vincristine, and vinorelbine), paclitaxel, epidipodophyllotoxins (e.g., etoposide, teniposide), antibiotics (e.g., dactinomycin, actinomycin D, daunorubicin, doxorubicin and idarubicin), anthracyclines, mitoxantrone, bleomycins, plicamycin, mithramycin and mitomycin, enzymes (L-asparaginase, which systemically metabolizes L-asparagine and deprives cells which do not have the capacity to synthesize their own asparagine), antiplatelet agents such as G(GP) IIb/IIIa inhibitors and vitronectin receptor antagonists, anti-proliferative/antimitotic alkylating agents such as nitrogen mustards (e.g., mechlorethamine, cyclophosphamide and analogs, melphalan, chlorambucil), ethylenimines and methylmelamines (e.g., hexamethylmelamine and thiotepa), alkyl sulfonates-busulfan, nitrosoureas (e.g., carmustine (BCNU) and analogs, streptozocin), trazenes-dacarbazinine (DTIC), anti-proliferative/antimitotic antimetabolites such as folic acid analogs (e.g., methotrexate), pyrimidine analogs (e.g., fluorouracil, floxuridine, cytarabine), purine analogs and related inhibitors (e.g., mercaptopurine, thioguanine, pentostatin and 2-chlorodeoxyadenosine {cladribine}), platinum coordination complexes (e.g., cisplatin, carboplatin), procarbazine, hydroxyurea, mitotane, aminoglutethimide, hormones (e.g., estrogen), anti-coagulants (e.g., heparin, synthetic heparin salts and other inhibitors of thrombin), fibrinolytic agents (e.g., tissue plasminogen activator, streptokinase and urokinase), aspirin, dipyridamole, ticlopidine, clopidogrel, abciximab, antimigratory, antisecretory (e.g., breveldin), anti-inflammatory: such as adrenocortical steroids (e.g., cortisol, cortisone, fludrocortisone, prednisone, prednisolone, 6α-methylprednisolone, triamcinolone, betamethasone, and dexamethasone), non-steroidal agents (e.g., salicylic acid derivatives such as aspirin, para-aminophenol derivatives such as acetominophen, indole and indene acetic acids (e.g., indomethacin, sulindac, etodalac), heteroaryl acetic acids (e.g., tolmetin, diclofenac, ketorolac), arylpropionic acids (e.g., ibuprofen and derivatives), anthranilic acids (e.g., mefenamic acid, meclofenamic acid), enolic acids (e.g., piroxicam, tenoxicam, phenylbutazone, oxyphenthatrazone), nabumetone, gold compounds (e.g., auranofin, aurothioglucose, gold sodium thiomalate), immunosuppressives (e.g., cyclosporine, tacrolimus (FK-506), sirolimus (e.g., rapamycin, azathioprine, mycophenolate mofetil), angiogenic agents such as vascular endothelial growth factor (VEGF), fibroblast growth factor (FGF), angiotensin receptor blockers, nitric oxide donors, anti-sense oligionucleotides and combinations thereof, cell cycle inhibitors, mTOR inhibitors, and growth factor receptor signal transduction kinase inhibitors, retenoids, cyclin/CDK inhibitors, HMG co-enzyme reductase inhibitors (statins) or protease inhibitors, hypnotic/amnestic agents such as propofol, sodium thiopental, or the like, or a combination thereof.

A preferred biologically active agent is propofol. The biologically active agent may be used in amount of 0.3 to 20 wt %, preferably 0.4 to 15 wt % and more preferably 0.5 to 5 wt %, based on the total weight of the composition. In an exemplary embodiment, the biologically active agent is present in an amount of 0.75 to 2 wt %, based on the total weight of the composition. In an embodiment, the biologically active agent may be present in a weight ratio of 0.1:1 to 1:0.1 with respect to the sum of the fatty acid and the base oil.

In addition to the water, the biologically active agent, the fatty acid and the base oil, the composition may contain one or more surfactants. The composition may contain a non-ionic surfactant in addition to an ionic surfactant. Suitable non-ionic surfactants are PLURONIC (Polaxamers), TWEEN (Polysorbate), BRIJ (Polyoxyethylene glycol alkyl ether), and other GRAS surfactants. The surfactants is present in an amount of 0.5 to 10 wt %, preferably 1 to 5 wt %, based on the total weight of the composition. The composition may also contain surface active biosurfactants such as phospholipids.

In one embodiment, in one manner of manufacturing the composition, the water, the biologically active agent, the fatty acid and the base oil are mixed together to form an emulsion. The mixing may be conducted in devices that impart shear force, extensional force, compressive force, ultrasonic energy, electromagnetic energy, thermal energy or combinations comprising at least one of the foregoing forces or forms of energy. The mixing is conducted in processing equipment wherein the aforementioned forces are exerted by a single screw, multiple screws, intermeshing co-rotating or counter rotating screws, non-intermeshing co-rotating or counter rotating screws, reciprocating screws, screws with pins, barrels with pins, rolls, rams, helical rotors, or combinations comprising at least one of the foregoing. Blending involving the aforementioned forces may be conducted in machines such as single or multiple screw extruders, Buss kneader, Henschel, helicones, Ross mixer, Banbury, roll mills, Waring blender, or the like, or combinations comprising at least one of the foregoing machines. The mixing is preferably conducted in a Waring blender. Ultrasonication is also preferably used to prepare the emulsion.

The droplets (average domain particle size) of the emulsion are preferably 50 nanometers to 2 micrometers, preferably 100 nanometers to 1 micrometer. The particle size is determined by the particle diameter using dynamic light scattering.

In one embodiment, by using the base oil and the fatty in the composition, the amount of the biologically active agent in the aqueous (water) phase is less than 80 wt %, preferably less than 50 wt %, and more preferably less than 20 wt % of the amount with just the base oil or just the fatty acid present in an otherwise identical composition at the same total oil (the sum of the fatty acid and the base oil) loading.

The amount of the propofol present in the free form in the aqueous phase of the composition is less than 30 milligrams per liter of the aqueous phase, preferably less than 20 milligrams per liter of the aqueous phase and more preferably less than 10 milligrams per liter of the aqueous phase.

The droplets are stable for a period of over 1 year on the shelf at room temperature. In other words, the droplets are stable and do not undergo size changes when stored on a shelf at room temperature (23° C.) for a period of up to one year. In one embodiment, the droplets change in average domain particle size by less than 20%, preferably less than 15%, preferably less than 10% and more preferably by less than 5% when stored on a shelf at room temperature (23° C.) for a period of up to one year. In addition, the amount of the propofol present in the free form in the aqueous phase of the composition remains less than 30 milligrams per liter of the aqueous phase, preferably remains less than 20 milligrams per liter of the aqueous phase and more preferably remains less than 10 milligrams per liter of the aqueous phase when stored on a shelf at room temperature (23° C.) for a period of up to one year.

The following non-limiting example demonstrates the composition and the method of making the composition.

Example

This example was conducted to demonstrate the composition and the method of making the composition. Propofol USP (the biologically active agent) was donated by Albemarle Corporation (Baton Rouge, La., U.S.A.) and Diprivan was provided by Nanomedex, Inc. (Middleton, Wis., U.S.A.). Generally regarded as safe (GRAS) excipient oils including soybean oil, olive oil, castor oil, canola oil, ethyl butyrate, isopropyl myristate, isopropyl palmitate, and octanoic acid were all obtained from Fisher Scientific (Hampton, N.H., U.S.A.). Other vegetable oils including food grade canola oil and extra virgin olive oil were purchased at the local Publix grocery store (Lakeland, Fla., U.S.A.). All oils were used as received. Dulbecco's phosphate buffered saline (PBS), sodium caprylate, Pluronic F68, Tween 80, and Brij 80 were obtained from Sigma-Aldrich (St. Louis, Mo., U.S.A.). Sodium stearate was obtained from Alfa Aesar (Ward Hill, Mass., U.S.A.).

The base oils used are soybean oil, olive oil, castor oil, and canola oil while the fatty acids (or esters thereof) are ethyl butyrate, isopropyl myristate, isopropyl palmitate, and octanoic acid. Non-ionic surfactants are Pluronic F68, Tween 80, and Brij 78, while sodium stearate was used as the ionic surfactant.

Emulsions were prepared with 1 wt % propofol USP, 10 wt % of various GRAS oils (soybean oil, olive oil, castor oil, canola oil, ethyl butyrate, isopropyl myristate, isopropyl palmitate, and octanoic acid), various concentrations of nonionic surfactants (Pluronic F68, Tween 80, and Brij 78), and various concentrations of sodium stearate. In some cases, salt was added to explore ionic effects and glycerol was added to control the osmolarity without increasing ionic strength. The compositions of various emulsions explored here are summarized in Table 1, where the experiments focusing on a specific issue are grouped together into Groups 1-8. The purpose of the experiments in each group is also briefly included in the Table 1. For each formulation, the desired oil and drug were added in their proper mass ratios to 20 mL glass vials and mixed until homogenous. Concentrated stock surfactant solutions were separately prepared. 15 wt % Pluronic F68 was dissolved in DI water with magnetic stirring. Tween 80 and Brij 78 were used as received. Sodium stearate has limited aqueous solubility at room temperature; therefore a stock solution of 0.1 wt % sodium stearate was prepared in DI water and stirred at approximately 65° C. The concentrated surfactant solutions, glycerol, and any other desired component were added and diluted with DI water (qs). These oil and water mixtures were then sonicated using an ultrasonic probe sonicator (Fisher Scientific Sonic Dismembrator Model 100) with the probe tip set just below the oil-water interface for between 10-30 minutes. This process resulted in the formation of a homogenous milky white emulsion.

TABLE 1

| Group | Name | Stability Experiments Description | Excipient Oil | Nonionic Surfactant | Ionic Surfactant | Salt |
|---|---|---|---|---|---|---|
| 1 | Oil Type | Effect of oil type on emulsion stability | Various, 10 wt % total | 1 wt % Pluronic F68 | $10^{-3}$ and $10^{-4}$ wt % sodium stearate (SS) | None |
| 2 | Single vs. Binary Excipient Oils | Differences in emulsion stability with single and binary excipient oil type systems | Pure vegetable oil (soybean or olive) or binary mixtures of vegetable oil and ethyl butyrate (EB). 10 wt % total | 5 wt % Pluronic F68 | $10^{-4}$ wt % SS | None |
| 3 | Nonionic Surfactant Concentration | Effect of nonionic surfactant concentration on emulsion size and stability | Binary mixtures of vegetable oil (soybean or olive) and EB. 10 wt % total | 1 wt % and 3 wt % Pluronic F68 | $10^{-4}$ wt % SS | None |
| 4 | Nonionic Surfactant Type | Effect of nonionic surfactant type on emulsion size and stability | 5 wt % soybean oil (SO), 5% EB | 2 wt %, Pluronic F68, Tween 80, Brij 78 | $10^{-4}$ wt % SS | None |
| 5 | Zeta and Stability | Effect of ionic strength and pH on zeta potential and emulsion stability with and without surfactant | 10 wt % SO | None or 1 wt % Pluronic F68 | None | Up to 5 wt % NaCl, 0.01M HCl, and 0.01M NaOH |
| 6 | Ionic Strength | Effect of ionic strength on emulsion stability | 10 wt % SO or 5 wt % SO and 5% EB | 1 or 2 wt % Pluronic F68 | $10^{-4}$ wt % SS | 0.45-5 wt % NaCl, or PBS |
| 7 | High Conc Ionic Surfactants | Effect of higher concentrations of ionic surfactants | 10 wt % SO or 5 wt % SO and 5% EB | 2 wt % Pluronic F68 | 0.01 wt % and 0.05 wt % SS or 0.5 wt % and 5 wt % sodium caprylate | None |
| 8 | No Ionic Surfactants | Stability without the effect of ionic surfactants | 10 wt % SO | 2 wt % Pluronic F68 or Tween 80 | None | None |

About 10 mL of each emulsion was placed in a 20 mL vial and left undisturbed on a lab bench to explore each emulsion's stability to creaming. Creaming is an instability mechanism where lower density oil droplets rise to the top of the system forming a cream layer with a more clear serum layer below. The emulsions were photographed periodically with a digital camera (Panasonic DMC FH25), and the photographs were analyzed using image processing software (ImageJ) to quantify the degree of creaming. The height of each emulsion phase was measured in number of pixels, and the percentage serum was calculated from the serum height divided by the total emulsion height. The time at which creaming was first observed was used as a measure of each emulsion's stability, and the time at which the emulsion had completely creamed was noted if applicable. A creaming time longer than two years is desired to be considered a commercially viable pharmaceutical emulsion.

Propofol emulsions with low drug concentrations in the aqueous phase are desirable due to the potential correlation between free drug concentration and pain on injection. The free drug concentration in the aqueous phase of different emulsions can be determined based on the measured partition coefficient of the excipient oil used. To validate the partitioning data, the aqueous phase drug concentration was measured for a few emulsions using a dialysis method. Emulsions were placed in a well-rinsed 12-14 kDa MWCO dialysis bag (Fisher Scientific). The dialysis bag was then suspended into isotonic dialysis media at a 5:1 ratio of dialysis media to emulsion. The dialysis media was a solution of 2.25 wt % glycerol in DI water which matched the osmotic pressure of emulsion samples. Care was taken to ensure that the dialysis bags did not leak into the dialysis media. Samples were taken from the dialysate at time intervals to obtain transient free drug concentration data, and a final free drug concentration was observed when the free concentration no longer changed. Dialysate samples were analyzed with HPLC as well. However, this approach can only be used for relatively stable emulsions. Excipient oils in the emulsions must also have low aqueous solubility to ensure that they are retained in the dialysis bag.

Droplet Size Distributions

Droplet size distributions of emulsions were obtained using dynamic light scattering (DLS, Malvern Zetasizer Nano-ZS). Size measurements were conducted at various times after emulsion preparation to quantify emulsion stability. In some cases where emulsions had creamed, size distributions were measured for both serum and cream phases. Often the emulsions were too concentrated to give reliable droplet size measurements, therefore emulsions were diluted 10:1 (v/v) with DI water to prevent multiple scattering effects. DLS also provides the emulsion polydispersity index (PDI) between 0 and 1, a measurement of the uniformity of emulsion droplets. Low polydispersity index values (PDI=0.1 and below) indicate a very uniform droplet size range and are an indication of a stable emulsion. The greater amount of polydispersity, the more variable the droplet sizes obtained which can be an indication of several destabilizing mechanisms such as flocculation, coalescence, or phase separation.

Zeta Potential

Zeta potential measurements of formulations were obtained using electrophoretic light scattering (also Malvern Zetasizer Nano-ZS). Samples were diluted 20:1 (v/v) with identical aqueous phase solutions to minimize changes in conductivity. Smoluchowski fitting was used for these experiments since the Debye lengths are smaller than the emulsion droplet radii. However, in some cases, low ionic strength formulations may actually have comparable Debye lengths and droplet radii leading to some inaccuracies in the zeta potential measurements.

Freeze-Thaw Cycling

Freeze-thaw cycling was used as another method to quantify emulsion stability in addition to creaming and size distribution studies. Emulsions were frozen and thawed several times after formulation in attempt to exacerbate emulsion destabilization. Visual observations and droplet size measurements were taken after freezing and thawing each emulsion prepared several times. For each freeze-thaw cycle, emulsions were placed in a standard freezer at −18° C. for 16 hours, followed by 8 hours of thawing at room temperature.

Results and Discussion

The pain accompanying propofol injection is likely caused by the interaction of the drug with endothelial cells of the vasculature. Immediately after injection, the aqueous phase of the emulsion will come into contact with venous tissue, therefore, decreasing the amount of drug partitioned in the emulsion aqueous phase is a key design target for formulating an improved propofol emulsion. An optimal emulsion formulation for intravenous injection of propofol should have a high partitioning of the drug in the oil phase resulting in a low aqueous phase drug concentration. The optimal formulation should also be as shelf-stable as possible. All macroemulsions are thermodynamically unstable, but it is possible to design kinetically-stable systems with prolonged shelf life. To achieve the dual goals of low aqueous drug concentration and high kinetic stability, the formulation must be optimized by choosing suitable excipient oils and surfactants. In this study, eight oils from a list of GRAS oils (soybean oil, olive oil, castor oil, canola oil, ethyl butyrate, isopropyl myristate, isopropyl palmitate, and octanoic acid). Several nonionic surfactants (Pluronic F68, Tween 80, Brij 78) and ionic surfactants (sodium stearate, sodium caprylate) are also explored. The results on the partitioning of the drug in various oils, followed by studies on emulsion formulation and stability are presented below. The studies on emulsion stability are broadly divided into effects of excipient oils, nonionic surfactants, and finally ionic effects.

Drug Partitioning in Various Candidate Excipient Oils

Oil-water partition coefficients were calculated by equilibrating a mixture of propofol, water, and oil with mass fractions $f_{drug}$, $f_{aq}$, and $f_{oil}$, respectively. The drug loading was kept constant at 1 wt %, while oil loadings were chosen to be 5 or 15 wt %. Additional experiments were performed at 10 wt % excipient oil loading for ethyl butyrate and soybean oil because of the major focus on these oils in this work. The water phase was separated and assayed for propofol concentration ($c_f$), and the partition coefficient was obtained from a mass balance, i.e., $$M_{drug} = V_{aq} c_f + K V_{oil} c_f \qquad (2)$$

where K is the oil-water partition coefficient, $M_{drug}$, $V_{aq}$ and $V_{oil}$ are the mass of oil and volumes of water and oil, respectively in the system. The mass balance yields the following equation for K:

$$K = \frac{f_{drug} - \dfrac{f_{aq} c_f}{\rho_{aq}}}{\dfrac{f_{oil} c_f}{\rho_{oil}}} \qquad (3)$$

where $\rho_{aq}$ and $\rho_{oil}$ are the densities of water and oil, respectively. Table 2 lists the molecular weight and densities of various oils considered, along with measured aqueous phase drug concentrations and calculated logarithmic oil-water partition coefficients.

TABLE 2

| Excipient Oil Type | Mw Excipient Oil (g/mol) | Oil Density (g/mL) | 5% Excipient Oil | | 10% Excipient Oil | | 15% Excipient Oil | |
|---|---|---|---|---|---|---|---|---|
| | | | $C_{free}$ (mg/L) | $\text{Log}_{10}K$ | $C_{free}$ (mg/L) | $\text{Log}_{10}K$ | $C_{free}$ (mg/L) | $\text{Log}_{10}K$ |
| Ethyl butyrate (EB) | 116.16 | 0.869 | 6.93 | 4.33 | 4.60 ± 1.83 | 4.32 | 2.48 | 4.35 |
| Octanoic acid (OA) | 144.21 | 0.898 | 33.5 | 3.65 | — | — | 10.0 | 3.76 |
| Isopropyl myristate (IM) | 270.45 | 0.843 | 16.9 | 3.92 | — | — | 4.39 | 4.08 |
| Isopropyl palmitate (IP) | 298.50 | 0.841 | 28.1 | 3.71 | — | — | 5.17 | 4.01 |
| Soybean oil (SO) | 874 | 0.909 | 51.2 | 3.48 | 19.12 ± 3.80 | 3.65 | 12.6 | 3.66 |

The drug concentration in the aqueous phase decreases with increasing oil loading as a higher fraction is retained in the oil phase. Due to dilute drug conditions, the partition coefficient is independent of the oil loading. However, the partition coefficients vary significantly with different excipient oils with a clear dependence on the molecular weight of the oil. Among the excipient oils considered, ethyl butyrate with the lowest molecular weight and soybean oil with the highest molecular weight had log(K) values of 4.3 and 3.6, respectively. It is clear excipient oil type and concentration are both important when considering the aqueous phase concentration of drug in emulsion formulations.

Direct Measurement of the Aqueous Phase Propofol Concentration in Emulsion

Figure 1:
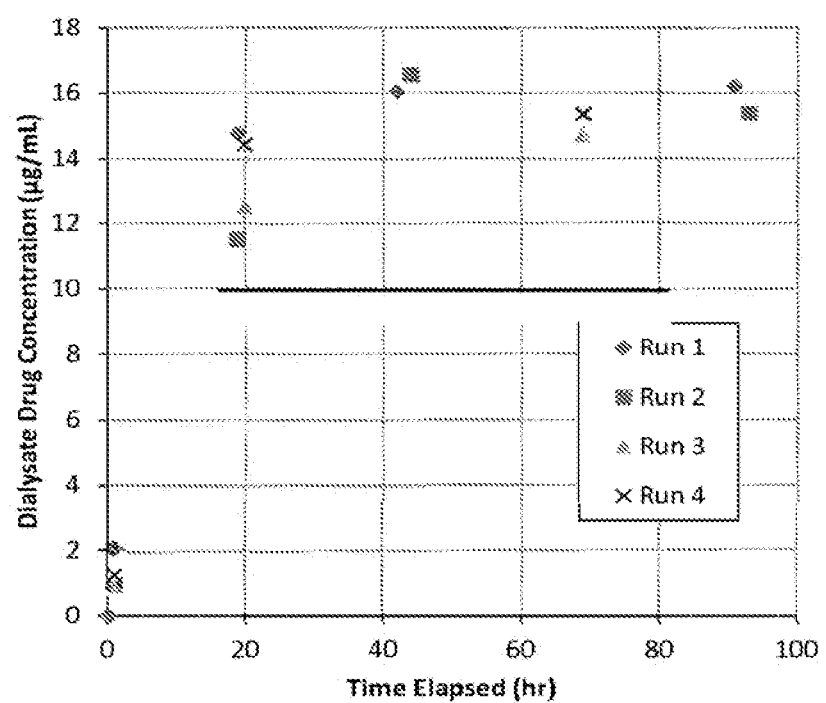
FIG. 1 is a graph showing the evolution of propofol concentration in dialysate over time for several emulsions of 1 wt % propofol and 10 wt % soybean oil.

The aqueous phase drug concentrations reported above were obtained by equilibrating drug with bulk water and oil. The intravenous formulations of propofol are emulsions which contain surfactant molecules and dispersed droplets with large interfacial area in addition to the oil and water phases. Since propofol is not a surface active drug, its partitioning at the interface is not expected to significantly impact the distribution of drug into the oil and the water phases; the free drug concentrations in emulsion formulations should be equal to the aqueous concentrations in equilibrated oil-water systems. To validate this, the aqueous phase drug concentrations of several emulsions loaded with drug and soybean oil were measured with dialysis. Emulsions containing 10 wt % soybean oil, 1 wt % propofol and between 1-5 wt % Pluronic F68 surfactant were prepared and sealed in dialysis bags. The transient concentration in the dialysate was measured until equilibrium was achieved. The results of these experiments are shown in FIG. 1. The drug concentration in the dialysate begins to level off after approximately 40 hours. Once equilibrium is reached, the final drug concentration in the dialysate must be equal to the concentration in the aqueous phase of the emulsion. It should be noted that the dialysate volume was chosen to be sufficiently large to submerge the dialysis bag, but also sufficiently small so that only a small fraction of the drug loaded inside the dialysis bag diffuses out until equilibrium is achieved. The aqueous phase drug concentrations obtained from partition coefficient (19.1±3.8 mg/L) and dialysis experiments (16.2±1.8 mg/L) are in good agreement. These results indicate that the presence of emulsion droplets and surfactant have little effect on the equilibrium partitioning of drug between the excipient oils and the aqueous phase. Thus, the data for the aqueous phase concentrations obtained with bulk oil and water phases can be considered as equal to the free drug concentration in an emulsion formulation with the corresponding ratio of oil to water.

Drug Partitioning in Mixtures of Oils

Figure 2:
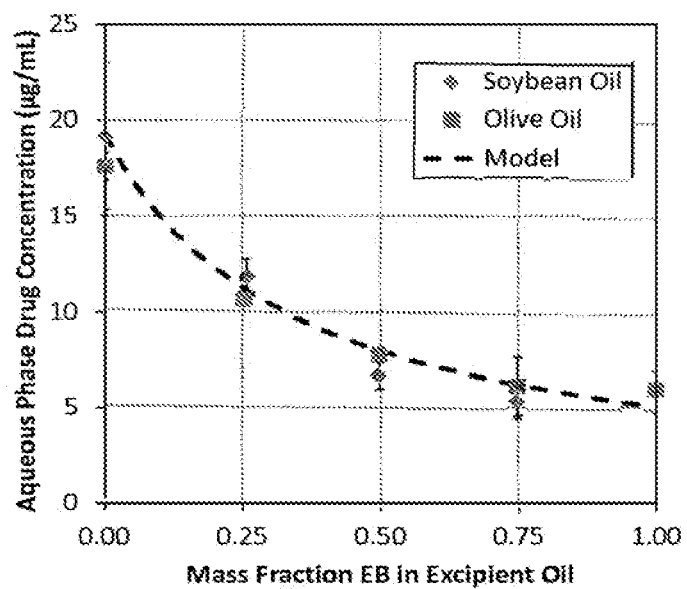
FIG. 2 is a graph showing free drug concentration from systems with binary excipient oil mixtures of soybean oil and ethyl butyrate or olive oil and ethyl butyrate.

We greatly reduced the emulsion design space by eliminating several candidate excipient oil compounds due to poor drug partitioning and emulsion stability which will be shown in following sections. Interestingly, even though the pure ethyl butyrate emulsions are highly unstable, a 50:50 mixture of soybean oil and ethyl butyrate was very stable. We hypothesized that this binary mixture of excipient oils would reduce the aqueous drug concentration somewhere between the values obtained with pure soybean oil and pure ethyl butyrate. If the binary mixture of excipient oils also reduced the free drug concentration, it would be a very ideal formulation for propofol delivery. Experiments were performed to measure the drug partitioning of binary mixtures of excipient oils. 1 wt % drug loading and 10 wt % total excipient oil loading were maintained as the experimental basis of all the binary systems formed to compare with Diprivan. The relative fractions of excipient oil were varied between 100 wt % ethyl butyrate and 100 wt % soybean oil. FIG. 2 shows the aqueous phase drug concentrations of mixtures of drug, binary excipient oils, and water. These experiments were repeated by replacing soybean oil with olive oil.

Figure 3:
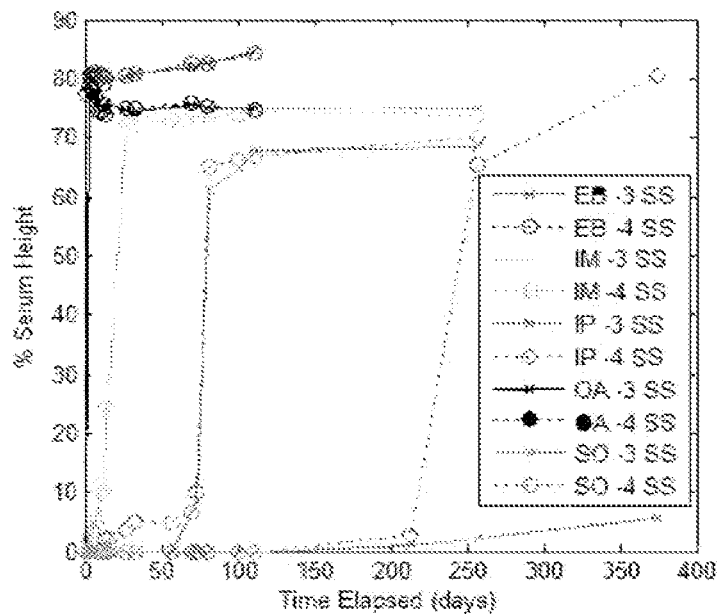
FIG. 3 is a graph showing creaming heights over time of emulsions prepared with a single excipient oil type.

As the portion of ethyl butyrate increases, the aqueous phase drug concentration reduces significantly. By assuming ideal mixing of ethyl butyrate, soybean oil, and the drug in the oil phase, a drug mass balance gives the following equation:

$$M_{drug} = V_{aq}C_f + (K_{EB}V_{EB} + K_{SO}V_{SO})c_f \quad (4)$$

where EB and SO represent ethyl butyrate and soybean oil, respectively. The dashed line in FIG. 2 is the best fit curve to the above equation with values of 19,900 and 5,200 for $K_{EB}$ and $K_{SO}$, respectively. The model fits are in good agreement with the experimental data. A 50:50 mixture of ethyl butyrate and either soybean or olive oil reduces the aqueous drug concentration by over half when compared with the pure vegetable oil excipient. Therefore, emulsion systems with 1 wt % drug, 5 wt % ethyl butyrate, and 5 wt % triglyceride vegetable oils (soybean or olive) were selected as the design goal. Unfortunately, the aqueous drug concentration of binary excipient oil emulsions could not be confirmed with dialysis because ethyl butyrate also diffuses out into the dialysate due to its relatively high water solubility and small molecular weight. Additionally, the volatility of ethyl butyrate decreased the accuracy of concentration measurements with dialysis of binary oil mixtures.

Effect of Excipient Oil on Emulsion Stability

Emulsion stability depends on various factors including the type and loading of oil and surfactant, formulation pH, temperature, and salinity. To explore the effect of oil on emulsion stability (Group 1 in Table 1), emulsions were prepared with 1 wt % drug (Propofol) loading and 10 wt % of various excipient oil compounds. Each formulation was prepared with 1 wt % nonionic Pluronic F68 surfactant. Each excipient oil formulation was prepared with two concentrations ($10^{-3}$ wt % and $10^{-4}$ wt %) of sodium stearate. The concentrations of sodium stearate were kept very low because ionization of the surfactant will increase the solution ionic strength which reduces electrostatic repulsions. This issue is discussed in greater detail later. Assuming sodium stearate completely dissociates, the Debye length for $10^{-3}$ wt % and $10^{-4}$ wt % SS solutions are 53 and 166 nm, respectively, compared to 962 nm for DI water. At higher concentrations the Debye length may be far too small to achieve significant electrostatic effects. It is however noted that due to stearic acid's low pKa of about 4.9, only a small fraction of stearate at the interface will be in the ionized form at biological pH.

Initial Oil Screening

Preliminary screening of emulsion stability was conducted by leaving emulsions undisturbed on a shelf and making visual observations at various times. The initial images of the two formulations for each of the five excipient oils are included in the top row of FIG. 3. Ethyl butyrate emulsions showed very rapid phase separation even before images could be acquired showing that these emulsions are highly unstable. While ethyl butyrate exhibits the highest drug partitioning, it demonstrates poor emulsion stability. Thus, emulsions with ethyl butyrate alone as excipient oil are not suitable for intravenous delivery of propofol. Since it was immediately realized that ethyl butyrate emulsions are highly unstable, a 50:50 mix of ethyl butyrate and soybean oil as the excipient (5 wt % each) was also included in the preliminary screening studies in addition to the five pure oil systems. All the emulsions systems except pure ethyl butyrate appear homogeneous, opaque, and white just after formation. Visual observations of the emulsions showed that within a year, all emulsions except soybean oil and the 50:50 mix of soybean oil and ethyl butyrate separated into two layers comprising of a clear lower serum layer and an upper opaque cream layer. The serum phase is mostly water, and the cream phase appears to be an emulsion with higher oil loadings compared to the starting value. After long times however, the cream layer can completely destabilize leaving an unemulsified oil layer at the top.

Images of the emulsions were digitally measured to determine the serum height as a function of time for all the emulsion systems (FIG. 3). A stable system should not separate into cream and serum phases, so the time at which serum is first observed is considered to be an approximate indicator of the degree of stability. Plots of serum heights over time show that despite reducing aqueous phase drug concentrations further, lower molecular weight excipient oils suffered from poor emulsion stability tending to rapidly phase separate after sonication. Intermediate oils such as isopropyl myristate and isopropyl palmitate required several days or weeks to begin creaming, while the larger triglyceride oils tended to remain stable to creaming. The results also showed very little difference in creaming between $10^{-4}$ wt % and $10^{-3}$ wt % sodium stearate likely due to small concentrations and the low pKa of stearic acid.

The plots of serum heights as a function of time (FIG. 3) are highly non-linear with an initial stable phase during which the emulsions appear to be homogeneous with no observable separation followed by rapid creaming. FIG. 3 shows creaming heights over time of emulsions prepared with a single excipient oil type. Once the serum appears, the rate of creaming accelerates. Complete creaming occurs in a fraction of the time that it took for the first onset of creaming. The increase in creaming rates could potentially be due to aggregation forming larger size droplets that have a greater rising velocity.

Figure 4A:
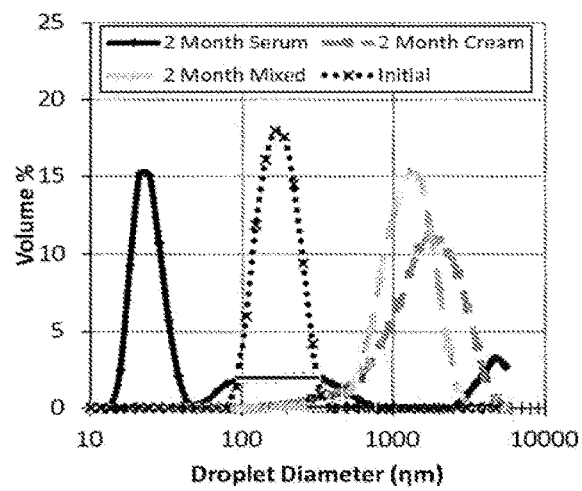
FIG. 4(A) is a graph showing volume droplet size distributions of serum and cream phases of 10 wt % isopropyl myristate, 3 wt % Pluronic F68, and 0.1 wt % sodium stearate emulsion.

To better understand creaming dynamics, size distributions were measured in the serum and cream layers for two of the emulsion systems, isopropyl myristate and soybean oil. Emulsions of isopropyl myristate reached serum heights of over 70% in less than two months, while those of soybean oil exhibited less than 10% serum height after thirteen months. FIG. 4(A) shows size distributions in the cream and serum for isopropyl myristate after two months of shelf life. The initial emulsion size distribution is included for comparison. The data shows that the droplet size in the cream layer is much larger than the original diameter, while the serum layer has droplets of smaller size. After mixing the serum and cream phases, the droplet size distribution remains similar to the cream phase indicating an irreversible growth of droplet size has occurred. Additionally, visual transparency of the serum phase suggests a very small volume fraction of droplets. This data is consistent with the hypothesis that the cream layer is formed by droplet aggregation and coalescence which results in an increase in size and a consequent increase in the rising velocity. The size of the emulsions in the cream layer is ten times that of the starting size, which would imply a 100-fold larger rising velocity since settling velocity scales with the square of droplet size.

Figure 4B:
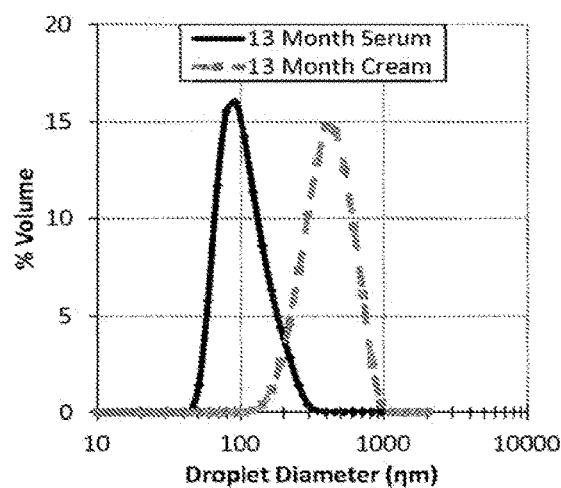
FIG. 4(B) is a graph showing volume droplet size distributions of serum and cream phases of a composition comprising 1 wt % propofol, 10 wt % soybean oil, 1 wt % Pluronic F68 and $10^{-3}$ wt % sodium stearate emulsion.

Conversely, size distributions of the serum and cream layers of a soybean oil formulation after 13 months of storage are shown in FIG. 4(B). The size in the cream layer is larger than that of the serum in this case as well, but the cream size distribution is very similar to the starting distribution suggesting negligible aggregation has occurred during the 13 months of storage. Essentially, the cream layer is an emulsion with a slightly higher oil loading compared to the original formulation, and it formed due to density differences between the oil and the continuous phases. The droplet sizes in the serum phase are significantly smaller than in the cream and may be due to surfactant micelles. There was no phase separation (oiling off) occurring in the soybean oil cream layer, which further suggests that the cream layer is still an emulsion. In this case, gentle shaking is sufficient to render the emulsion uniform with size distributions similar to the starting distribution. While soybean oil emulsions creamed about 10% after one year, the 50:50 mixture of soybean oil and ethyl butyrate did not exhibit any creaming even after 13 months in spite of the lower density of ethyl butyrate (0.869 g/mL) compared to soybean oil (0.909 g/mL) possibly due to smaller size of the oil droplets as discussed below.

Comparing Emulsion Stability with Pure Excipient Oils and Binary Mixture of Excipient Oils The creaming studies described above clearly show that emulsions of pure soybean oil and 50:50 mixtures of soybean oil and ethyl butyrate are stable for a long period of time. The binary mixture appears to be more stable as it did not exhibit any creaming in 13 months. The enhanced stability of the binary mixture emulsion compared of either of the oils is an unexpected result and shows that the emulsion stability is a complex phenomena impacted by several properties of the oils including bulk and viscosity, interfacial tension and elasticity, surface charge, etc. The inclusion of ethyl butyrate likely reduces the interfacial tension resulting in the improved stability. However pure ethyl butyrate does not form stable emulsions likely due to low viscosity and interfacial elasticity. Since soybean oil is actually a mix of several oily molecules, refining the soybean oil to removal a fraction of the large triglycerides could potentially have a similar effect as mixing of the natural soybean oil and ethyl butyrate. Below, these two systems (soybean oil emulsions and 50:50 mix of soybean oil and ethyl butyrate) are compared (Group 2 in Table 1) by measuring size distributions at various times during shelf storage and also after exposing freshly prepared emulsions to freeze-thaw cycles. Freeze-thaw cycling is commonly used as an accelerated method for testing the stability of emulsions. To be consistent with Diprivan, we again only consider systems with 10 wt % oil loading and 1 wt % propofol. As discussed above, the preliminary soybean oil emulsion exhibited some creaming in a year which is undesirable. Since creaming was attributed to rising of the larger oil droplets, it was hypothesized that increasing the surfactant concentration will reduce oil droplet size and minimize creaming. Accordingly, the emulsions discussed below were prepared with higher concentration of nonionic surfactant (5 wt %) to reduce the droplet size and very low concentration of ionic surfactant ($10^{-4}$ wt % sodium stearate). Each soybean oil emulsion was also replicated with olive oil in this group.

Figure 5A:
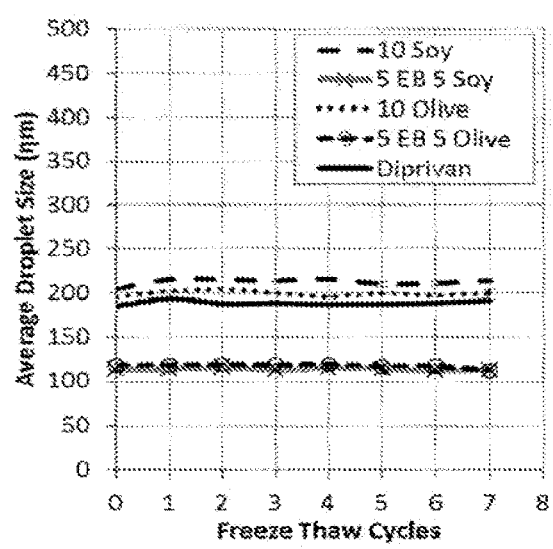
FIG. 5(A) is a graph showing average droplet sizes of emulsions with different excipient oil compositions after several freeze-thaw cycles.
Figure 5B:
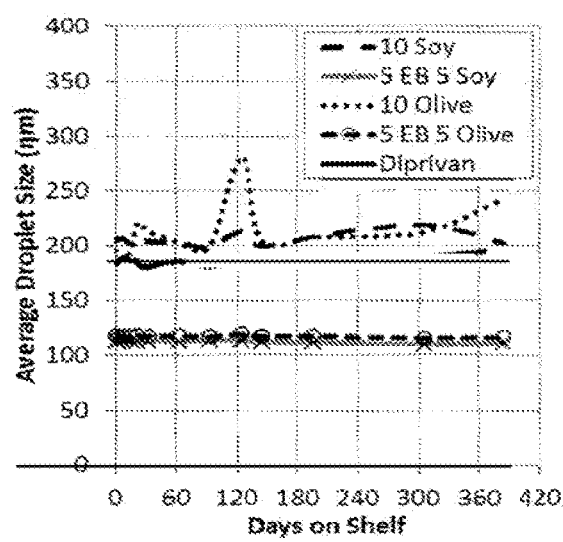
FIG. 5(B) is a graph showing shelf life for emulsions with different excipient oil compositions. All the compositions in the FIGS. 5(A) and 5(B) contain 1 wt % propofol, 5 wt % Pluronic F68, and $10^{-4}$ wt % sodium stearate.

The mean droplet sizes of the four emulsions and Diprivan after freeze-thaw cycling and shelf life are shown in FIG. 5(A)-5(B). The mean sizes remain unchanged for the entire duration of about a year for all of the systems. Also, each of the five emulsions remain stable to seven freeze-thaw cycles, which further suggest that these emulsion systems are kinetically stable. Comparing the mean size data for the soybean oil emulsions with the preliminary creaming study formulations (FIG. 4(B)) shows that increasing the surfactant loading from 1 wt % to 5 wt % reduces the droplet size by 27%. The mean sizes of the olive oil emulsions are comparable to soybean oil and Diprivan, but introducing ethyl butyrate significantly reduces the size for both olive and soybean oils. Also, the polydispersity index (PDI) decreases with inclusion of ethyl butyrate from 0.180 for pure oils to about 0.130 for the binary mixtures.

Thus, the benefits of including ethyl butyrate are twofold. Improved kinetic stability was observed for both soybean oil and olive oil with reduced droplet size and polydispersity. Adding ethyl butyrate also increases the partitioning of drug into the oil phase which reduces the aqueous phase drug concentration of the emulsion which may be useful to reduce patient pain and discomfort on injection. Based on these results, ethyl butyrate is considered a suitable additive to accomplish the design goals for an improved propofol formulation.

Effect of Nonionic Surfactant on Emulsion Stability

It has been shown that increasing the nonionic surfactant concentration from 1 to 5 wt % reduces the droplet size and improves stability. The effect of the concentration and type of the nonionic surfactant on emulsion properties is detailed below along with other nonionic surfactant compounds.

Surfactant Concentration

Figure 6A:
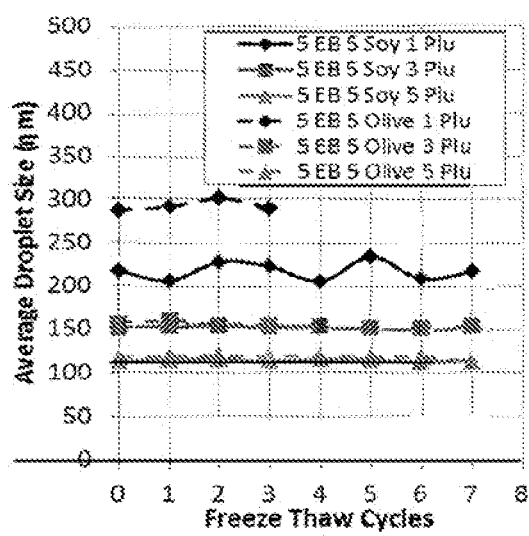
FIG. 6(A) is a graph showing average droplet sizes for the different emulsions after several freeze-thaw cycles.
Figure 6B:
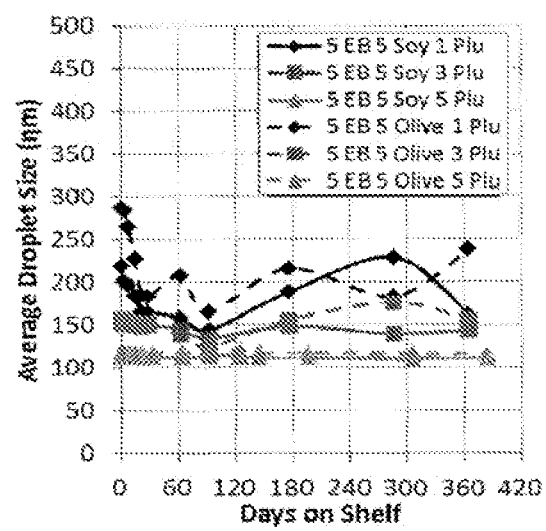
FIG. 6(B) is a graph showing shelf life for the emulsions of the FIG. 6(A). All formulations of the FIGS. 6(A) and 6(B) contain 1 wt % propofol, 5 wt % ethyl butyrate, and $10^{-4}$ wt % sodium stearate.

This example was focused on binary excipient oil mixtures (Group 3 in Table 1) with a total oil loading of 10 wt % and fix the drug and sodium stearate loadings at 1 and $10^{-4}$ wt %, respectively. FIGS. 6(A) and 6(B) show the changes in droplet size with freeze-thaw cycling and long term shelf life for surfactant loadings of 1 wt %, 3 wt %, and 5 wt % Pluronic F68. Larger amounts of nonionic surfactant yield smaller emulsion droplets with less variability in size and polydispersity after both freeze-thaw cycling and shelf life. Polydispersity index (PDI) ranges from 0.109 to 0.146 and 0.228 to 0.238 for 3 wt % and 1 wt % Pluronic formulations respectively. A sample lot of Diprivan was also included as a comparison (PDI value 0.066). The binary excipient oil formulations with 1 wt % Pluronic formed larger emulsion droplets than Diprivan, while 3 wt % Pluronic formed smaller droplets. Diprivan contains 1.2 wt % egg lecithin as a surfactant and includes only one excipient oil, 10 wt % soybean oil. These results show that the desired droplet size can be modified and controlled by altering the overall surfactant concentration. These results also showed olive oil formulations seemed more variable in size and polydispersity.

Surfactant Type

Figure 7A:
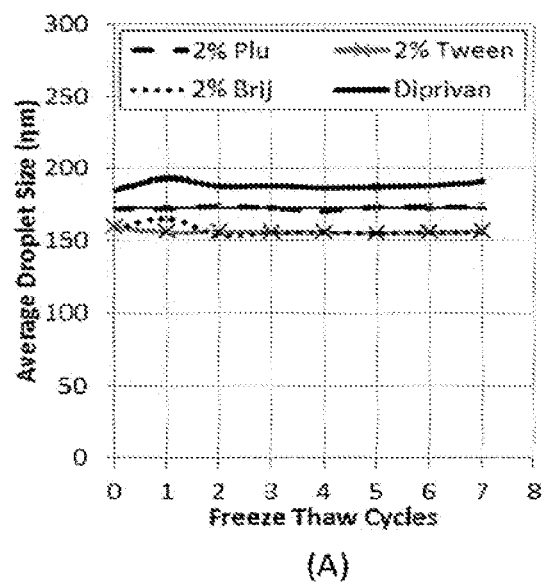
FIG. 7(A) is a graph showing average droplet sizes for the different emulsions after several freeze-thaw cycles.
Figure 7B:
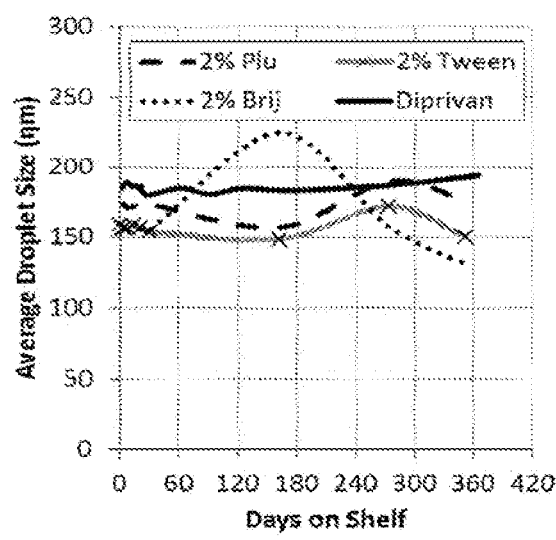
FIG. 7(B) is a graph showing shelf life for the emulsions of the FIG. 7(A). All samples in the FIGS. 7(A) and 7(B) contain 1 wt % propofol, 5 wt % soybean oil, 5 wt % ethyl butyrate, $10^{-4}$ wt % sodium stearate.

Several biocompatible nonionic surfactants were considered for the optimal propofol formulation (Group 4 in Table 1). The three nonionic surfactants were Pluronic F68, Tween 80, and Brij 78. Formulations of 1 wt % propofol, 5 wt % soybean oil, 5 wt % ethyl butyrate, and $10^{-4}$ wt % sodium stearate were prepared with 2 wt % of each of these nonionic surfactants. FIGS. 7(A) and 7(B) show little difference in droplet size obtained from the three different nonionic surfactants for freeze-thaw cycling and shelf life studies. Pluronic formulations show the lowest amount of polydispersity, but any difference seen is very small. PDI values obtained were 0.127, 0.202, and 0.174 for 2 wt % Pluronic, Tween, and Brij respectively.

These results suggest there are no major differences in effectiveness between the three nonionic surfactants considered for the proposed emulsion formulation. Additionally, 2 wt % of nonionic surfactant appears to have very similar droplet size to the Diprivan control formulation. Shelf life stability is comparable to the Diprivan control sample, thus 2 wt % nonionic surfactant (in particular Pluronic F68) is recommended for propofol emulsions.

In general, we have observed nonionic surfactant concentrations have a major effect on the droplet size. Among the formulations with stable excipient oils, increasing the nonionic surfactant concentration yielded an emulsion more resistant to creaming with reduced droplet size. However, increasing surfactant loading can introduce additional problems. In general, it is preferred to limit the amount of foreign compounds introduced to the body. Smaller emulsion droplets of propofol will likely dissolve more rapidly after injection resulting in elevated blood drug concentrations local to the injection site. Therefore an intermediate surfactant loading of 2-3 wt % is recommended.

Exploring Ionic Interactions and Effects

Up to this point, all emulsions considered contain a very small loading (0.0001-0.001 wt %) of the ionic surfactant sodium stearate. Only a very small fraction of this amount is expected to be in the anionic form due to the very low pKa of stearic acid. Thus, kinetic stability is likely not arising from ionic surfactants adsorbed at the interface. However, several studies suggest that Pluronics and other nonionic surfactants adsorb hydroxide ions at the interface. Other investigations demonstrate surface charge in oil and water systems without any surfactant. It is thus feasible that electrostatic interactions are important in these systems even though the concentration of ionic surfactant is negligible.

Zeta Potential

To investigate this possibility, mixtures of only 10 wt % soybean oil and aqueous solutions of various pH and ionic strengths were prepared. We then sonicated the mixture and measured the zeta potential and formulation stability. These experiments were repeated with 1 wt % Pluronic F68 added to the mixture. The results of these measurements (Group 5 in Table 1, Table 3) show that droplets of soybean oil in DI water have a highly negative zeta potential of −91.1 mV, which reduces to −30 mV in PBS and to a negligibly small value in 5 wt % NaCl solution. This proves that ions are adsorbing to the oil droplet interface, and this could play an important role in emulsion stability. On adding 0.01M HCl to deionized (DI) water, the zeta potential becomes −7.6 mV, which further suggests that hydroxyl ions are adsorbing to the oil-water interface. There is a strong correlation between the magnitude of zeta potential and emulsion stability without any surfactants, with the emulsions prepared in DI water remaining stable for about one day, while those in PBS and acid destabilizing very rapidly. However, the correlation between zeta potential and emulsion stability was not observed when 1 wt % Pluronic was included.

TABLE 3

| | | No Surfactant | | 1% Pluronic F68 | |
|---|---|---|---|---|---|
| Oil | Aqueous Phase | Zeta Potential ± σ (mV) | Days of Stability | Zeta Potential ± σ (mV) | Days of Stability |
| 10% Soybean oil | DI water | −91.1 ± 0.1 | 1-2 | −24.6 ± 0.7 | >365 |
| | PBS | −30.0 ± 0.2 | <1 | −1.0 ± 1.3 | >30 |
| | 5% wt NaCl | 0.8 ± 1.1 | <1 | — | <60 |
| | 0.01M HCl | −7.6 ± 0.5 | <1 | 0.2 ± 1.0 | >30 |
| | 0.01M NaOH | −47.7 ± 1.5 | >30 | −2.7 ± 0.7 | >30 |

Adding Pluronic surfactant to each of the systems considered significantly decreases the magnitude of zeta potential despite greatly increasing the stability of the mixtures. The decrease in the magnitude of the zeta potential could be due to a lower affinity for charge adsorption with Pluronic or possibly due to shifting of the slip plane further away from the surface where ions may adsorb. Thus, these results suggest electrostatic repulsions are not dominant in providing the long-term kinetic stability of emulsions as shown above. To further test the importance of ionic effects, the stability of the emulsions for a range of salt concentrations was explored.

Salt Effect

Figure 8A:
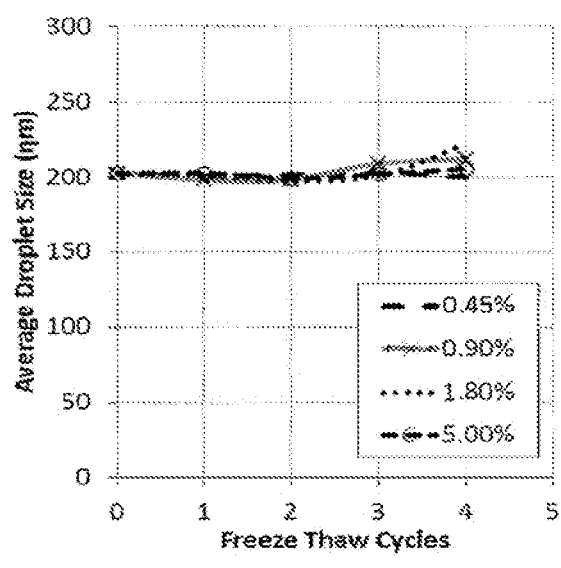
FIG. 8(A) is a graph showing average droplet sizes at different ionic strengths for the different emulsions after several freeze-thaw cycles.
Figure 8B:
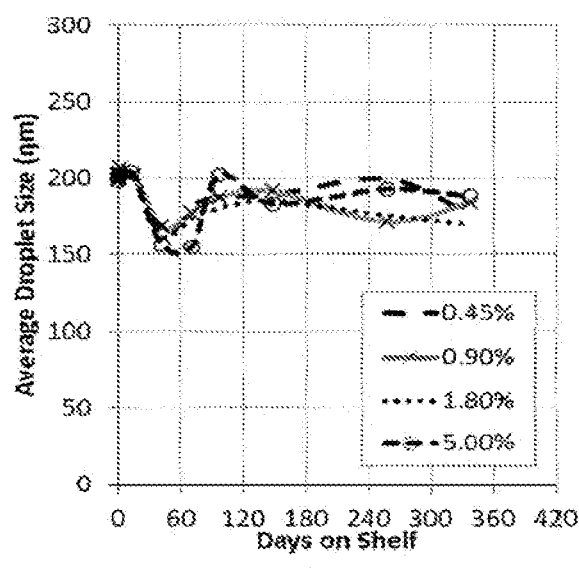
FIG. 8(B) is a graph showing shelf life for the emulsions of the FIG. 8(A). All emulsions of the FIGS. 8(A) and 8(B)

In these experiments, four different concentrations of sodium chloride (0.45 wt %, 0.9 wt %, 1.8 wt %, and 5 wt %) were added to a kinetically stable emulsion comprising of 1 wt % propofol, 5 wt % soybean oil, 5 wt % ethyl butyrate, 1 wt % Pluronic F68, $10^{-4}$ wt % sodium stearate (Group 6 in Table 1). Again, these emulsions were evaluated for stability with freeze-thaw cycling and shelf life (FIG. 8(A)-8(B)). The images (not shown) and the size distributions clearly show that the emulsions remain stable for longer than a year even for salt concentrations of 5 wt %. There was however some evidence of discoloration of the formulations starting at about 2 months which appears to be proportional to salt concentration. Discoloration may be due to dimerization of propofol which occurs spontaneously with exposure to oxygen. Elevated salt concentration may exacerbate the dimerization reaction, but this has no effect on the droplet size or stability of the emulsion. These studies prove that ionic effects are not important for emulsion stability even at low ionic surfactant concentrations. Next, we explore whether increasing the sodium stearate concentration can impact stability.

Effect of Sodium Stearate Concentration

We prepared emulsions with increased concentration of sodium stearate (0.01% and 0.05%) with fixed 1 wt % propofol, 10 wt % soybean oil, and 2 wt % Pluronic F68 (Group 7 in Table 1). These formulations were also subjected to freeze-thaw cycling and shelf life to assess their stability. The upper limit of sodium stearate concentration was limited to 0.05 wt % due to the low solubility limit of sodium stearate at room temperature. Formulations with sodium stearate concentrations approaching the solubility limit tend to partially solidify or gel when finely dispersed under sonication and cooled to room temperature. The photographs (not shown) of the emulsions with three loadings of sodium stearate ranging from $10^{-4}$ wt % to 0.05 wt % along with size measurements (data not shown) suggest that increasing the concentration of sodium stearate up to 0.05 wt % has little to no effect on emulsion stability. Finally, two emulsion formulations containing no ionic surfactant (Group 8 in Table 1) were made with 1 wt % propofol, 10 wt % soybean oil and 2 wt % nonionic surfactant (Pluronic F68 or Tween 80). The stability of these formulations was also tested with freeze-thaw cycling and shelf life and compared with the results for the formulations containing elevated sodium stearate concentration. The results of these experiments are shown in FIGS. 9 (A) and (B).

As expected, there was very little difference visually and quantitatively between formulations with no ionic surfactant and the proposed formulation indicating ionic surfactant is not necessary to achieve long-term kinetic stability of emulsions.

The results from this study show that emulsions containing 1 wt % drug and 10 wt % soybean oil, olive oil, and mixtures of these oils with ethyl butyrate can be designed to be kinetically stable for longer than a year by using 1-5 wt % of Pluronic F68, Tween 80 or Brij 78. While a low concentration of sodium stearate was used in most of the formulations, it was eventually concluded that the ionic effects play a negligible role in stability, and thus, sodium stearate can be removed from the formulation without impacting stability. The emulsion stability depends strongly on the oil type. Several other oils explored here including castor oil, canola oil, ethyl butyrate, isopropyl myristate, isopropyl palmitate, and octanoic acid did not yield stable emulsions with a correlation observed between stability and molecular weight of the excipient oil. Also, while pure ethyl butyrate emulsions are highly unstable, adding ethyl butyrate to soybean oil emulsions improved their stability. Ethyl butyrate also exhibits a high partition coefficient of the drug propofol with a partition coefficient of 19,900, which is about 4-fold higher compared to soybean oil. The free concentration of propofol in the aqueous phase of the emulsions is shown to decrease significantly by adding ethyl butyrate to the oil phase. As an additive, ethyl butyrate reduces the aqueous concentration of the drug in addition to improving emulsion stability, making it an optimal addition to the soybean oil based formulations of propofol. Based on all the results from this study, an emulsion comprising 1% wt propofol, 5% ethyl butyrate, 5% soybean oil and 3% Pluronic F68 displays excellent kinetic stability and greater than two-fold reduced aqueous concentration compared to Diprivan.

What is claimed is:

1. A method of manufacturing a composition comprising:
mixing a biologically active agent;
a first oil;
a second oil;
a non-ionic surfactant; and
water to form an emulsion; where the first oil and the second oil are present in the composition in an amount effective to reduce the amount of biologically active agent in an aqueous phase to less than 80 wt % of the amount with just the first oil present in an otherwise identical composition at the same total oil loading;
where the composition forms average domain particle size droplets of 100 nanometers to 1 micrometer as determined by dynamic light scattering;
where the biologically active agent is present in an amount of 0.5 to 5 wt %;
where the biologically active agent is selected from propofol, sodium thiopental, or any combination thereof;
where the first oil comprises at least one triglyceride and is present in an amount of 3 to 10 wt %;
where the second oil is a simple fatty acid or simple fatty acid ester and is present in an amount of 3 to 10 wt %;
where the non-ionic surfactant is present in an amount of 1 to 5 wt %;
where the non-ionic surfactant is selected from a poloxamer, a polysorbate, polyoxyethylene glycol alkyl ether, or any combination thereof;
where the water is present in an amount of 50 to 90 wt %; and
where the wt % is based on the total weight of the composition.

2. The method of claim 1, where the fatty acid and the first oil are present in a weight ratio of from 4:6 to 6:4.

3. The method of claim 1, wherein the first oil is selected from algae oil, soybean oil, olive oil, rapeseed oil, castor bean oil, sunflower seed oil, peanut oil, corn oil, safflower seed oil, linseed oil, jatropha oil, apricot seed oil, mango oil, coconut oil, cashew nut oil, or a combination thereof.

4. The method of claim 1, wherein the first oil is selected from alpha-linolenic acid, linoleic acid, oleic acid, stearic acid, palmitic acid, or any combination thereof.

5. The method of claim 1, where the first oil is soybean oil.

6. The method of claim 1, where the simple fatty acid is selected from methanoic acid, ethanoic acid, propanoic acid, butanoic acid, pentanoic acid, hexanoic acid, heptanoic acid, octanoic acid, nonanoic acid, decanoic acid, undecanoic acid, dodecanoic acid, tridecanoic acid, tetradecanoic acid, pentadecanoic acid, hexadecanoic acid, heptadecanoic acid, octadecanoic acid, icosanoic acid, or any combination thereof.

7. The method of claim 6, wherein the simple fatty acid is octanoic acid.

8. The method of claim 1, where the simple fatty acid ester is selected from allyl hexanoate, benzyl acetate, bornyl acetate, butyl acetate, butyl butyrate, butyl propanoate, ethyl acetate, ethyl butyrate, ethyl hexanoate, ethyl cinnamate, ethyl formate, ethyl heptanoate, ethyl isovalerate, ethyl lactate, ethyl nonanoate, ethyl pentanoate, geranyl acetate, geranyl butyrate, geranyl pentanoate, isobutyl acetate, isobutyl formate, isoamyl acetate, isopropyl acetate, linalyl acetate, linalyl butyrate, linalyl formate, methyl acetate, methyl anthranilate, methyl benzoate, methyl butyrate, methyl cinnamate, methyl pentanoate, methyl phenylacetate, methyl salicylate, nonyl caprylate, octyl acetate, octyl butyrate, amyl acetate, pentyl butyrate, pentyl hexanoate, pentyl pentanoate, propyl acetate, propyl hexanoate, propyl isobutyrate, terpenyl butyrate, or any combination thereof.

9. The method of claim 1, where the second oil is ethyl butyrate.

10. The method of claim 1, where the biologically active agent is propofol.

11. The method of claim 1, where the non-ionic surfactant is a poloxamer.

12. The method of claim 1, further comprising mixing an ionic surfactant with the biologically active agent; the first oil; the second oil; the non-ionic surfactant; and water to form the emulsion.

13. The method of claim 12, wherein the ionic surfactant is selected from sodium stearate, sodium caprylate, or a combination thereof.

14. The method of claim 13, where the sodium stearate is present in an amount of from 0.01 to 0.05 wt %.

15. The method of claim 1, further comprising sonicating the composition.

16. The method of claim 1, where the first oil is soybean oil and is present at 5 wt %, the second oil is ethyl butyrate and is present at 5 wt %, the biologically active agent is propofol and is present at 1 wt %, the non-ionic surfactant is a poloxamer and is present at 3 wt %, and the water is present at 86 wt %.

* * * * *